United States Patent
Treilhes et al.

(10) Patent No.: US 11,975,124 B2
(45) Date of Patent: May 7, 2024

(54) MULTILAYER SYNTHETIC RUBBER COMPOSITIONS

(71) Applicant: INEO-TECH SDN BHD, Pulau Pinang (MY)

(72) Inventors: Sebastien Treilhes, Gelugor (MY); Pierre Hoerner, Senlis (FR)

(73) Assignee: Ineo Tech Sdn Bhd, Pulau Pinang (MY)

( * ) Notice: Subject to any disclaimer, the term of this patent is extended or adjusted under 35 U.S.C. 154(b) by 399 days.

(21) Appl. No.: 17/312,377

(22) PCT Filed: Dec. 9, 2019

(86) PCT No.: PCT/MY2019/000047
§ 371 (c)(1),
(2) Date: Jun. 9, 2021

(87) PCT Pub. No.: WO2020/122704
PCT Pub. Date: Jun. 18, 2020

(65) Prior Publication Data
US 2022/0016322 A1     Jan. 20, 2022

(30) Foreign Application Priority Data

Dec. 10, 2018 (MY) .......................... PI 2018002449

(51) Int. Cl.
*A61L 31/04*     (2006.01)
*A61B 42/10*     (2016.01)
(Continued)

(52) U.S. Cl.
CPC ............ *A61L 31/049* (2013.01); *A61B 42/10* (2016.02); *A61L 31/041* (2013.01); *A61L 31/048* (2013.01);
(Continued)

(58) Field of Classification Search
CPC ..... A61L 31/049; B32B 27/32; B32B 27/302; C08L 53/02; C08L 23/00
See application file for complete search history.

(56) References Cited

U.S. PATENT DOCUMENTS

| | | | |
|---|---|---|---|
| 2004/0105943 A1* | 6/2004 | Hoerner | A61B 42/00 428/35.7 |
| 2008/0182093 A1 | 7/2008 | Sonntag et al. | |
| 2013/0316107 A1* | 11/2013 | Oleson | A41D 19/0055 524/427 |

FOREIGN PATENT DOCUMENTS

| | | |
|---|---|---|
| CN | 108587533 A | 9/2018 |
| EP | 0562088 A1 | 9/1993 |

(Continued)

OTHER PUBLICATIONS

International Search Report dated Apr. 22, 2020 corresponding to PCT/MY2019/000047 filed Dec. 9, 2019; 4 pages.
(Continued)

*Primary Examiner* — Prashant J Khatri
(74) *Attorney, Agent, or Firm* — Mintz, Levin, Cohn, Ferris, Glovsky and Popeo, P.C.

(57) ABSTRACT

Provided are multilayer synthetic rubber compositions formed from a layer of a styrene block copolymer composition and a layer of one or more synthetic elastomers, such as polychloroprene, polyisoprene, nitrile rubber, styrene butadiene rubber, butyl rubber and polyurethane. The multilayer compositions find use in the manufacture of thin walled articles, for example gloves, particularly medical or industrial gloves.

19 Claims, 1 Drawing Sheet

(51) Int. Cl.
  *A61L 31/06* (2006.01)
  *A61L 31/14* (2006.01)
  *C08L 11/00* (2006.01)
  *C08L 53/02* (2006.01)

(52) U.S. Cl.
  CPC .............. *A61L 31/06* (2013.01); *A61L 31/141* (2013.01); *A61L 2420/06* (2013.01); *A61L 2420/08* (2013.01); *C08L 11/00* (2013.01); *C08L 53/02* (2013.01)

(56) References Cited

FOREIGN PATENT DOCUMENTS

| EP | 1707596 A1 * | 10/2006 | ............ C08F 297/04 |
|----|---|---|---|
| FR | 2911991 A1 | 8/2008 | |
| NL | 2007262 C2 | 2/2013 | |
| WO | 1993/006996 A1 | 4/1993 | |
| WO | 02/02321 A1 | 1/2002 | |
| WO | WO-2008087675 A1 * | 7/2008 | ............ C08K 5/103 |
| WO | 2012/099853 A1 | 7/2012 | |
| WO | 2013/025440 A1 | 2/2013 | |

OTHER PUBLICATIONS

Written Opinion of the International Search Authority dated Apr. 22, 2020 corresponding to PCT/MY2019/000047 filed Dec. 9, 2019; 7 pages.

* cited by examiner

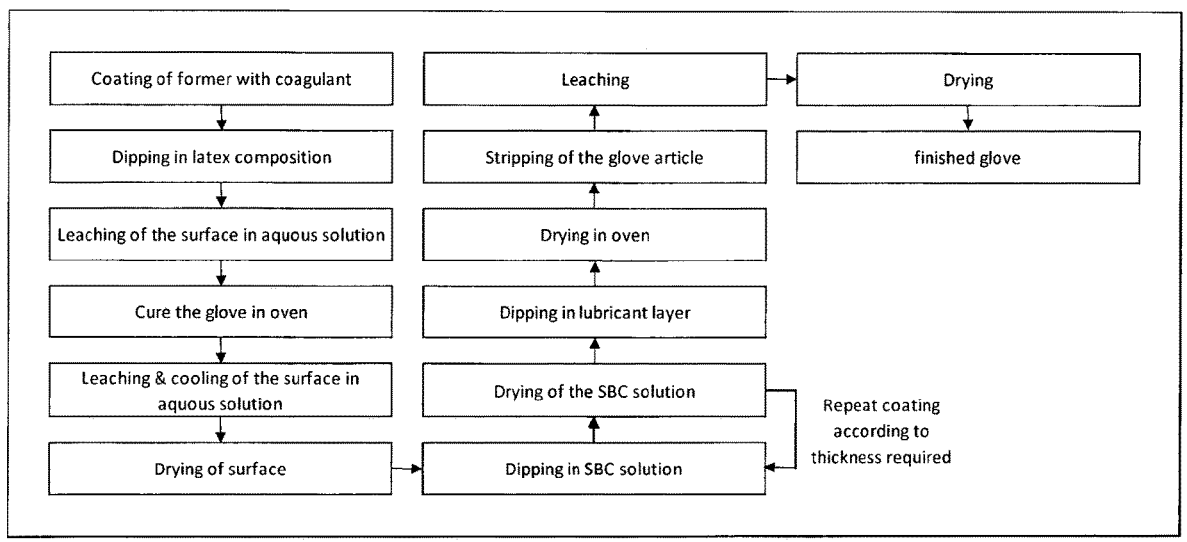

MULTILAYER SYNTHETIC RUBBER COMPOSITIONS

FIELD

This disclosure generally relates to multilayer synthetic rubber compositions formed from a layer of a styrene block copolymer composition and a protective layer of one or more synthetic elastomers, such as polychloroprene, polyisoprene, nitrile rubber, styrene butadiene rubber, butyl rubber and polyurethane. The multilayer compositions find use in the manufacture of thin walled articles, for example gloves, particularly medical or industrial gloves.

BACKGROUND

Gloves are used as a protective equipment in many applications, for example medical, industrial or household. Each of these applications has its own set of requirements that range from cut, tear, abrasion or puncture resistance, stretch-ability, enhanced grip-ability, flexibility, physical and chemical barrier properties, to cite only a few.

Particularly for surgical gloves, it is important that the gloves have high resistance to tear while remaining very flexible and safe for the skin.

To fulfil these requirements, the most commonly used materials are natural rubber latex (NR), polychloroprene (CR), polyisoprene (IR) and nitrile rubber (NBR).

These materials are formulated with various chemicals and additives to adjust their properties and performances. For example, vulcanization is the traditional chemical crosslinking mechanism for most elastomeric materials such as NR or IR. Vulcanization creates sulphur covalent bonds that link one polymer chain to another.

Since vulcanization with sulphur alone requires reaction conditions that are too long and at very high temperatures, chemical additives such as "accelerators" are added. Accelerators may be of many types and are usually classified within the following families: thiazoles, carbamates, guanidines, thiourea and thiurams. It is common practice to use a mixture of different accelerators selected from the different families to optimize the vulcanization speed and performance.

However, whereas sulphur is integrated into the polymer network through covalent bonding, accelerators are not. A typical glove formulation made of IR can comprise up to 2% of accelerators. The accelerator molecules have poor solubility in water and cannot be removed from the glove by leaching. Also, they may "bloom" at the surface of the film over time, due to their limited compatibility with the rubber.

When the glove is in use, the material is placed in direct contact with the hand skin. This is particularly the case for surgical usage, where the glove could be worn for prolonged times under occlusive conditions. It raises the issues of safety and biocompatibility of the material, as the various residual chemicals that are extracted during use can cause allergic reaction and skin problems. The most serious of these reactions to gloves, latex allergies from natural rubber gloves (also called immediate type 1 reactions), can be addressed by the use of synthetic alternatives to natural rubber such as IR, CR and NBR.

However, other critical issues remain with synthetic gloves: for instance, allergic contact dermatitis (called type IV reaction) caused by chemical accelerator residues as well as by other processing additives such as abietane related compounds (rosin resin) today represent a growing concern for healthcare workers. Chemical residues from surgical gloves can also create numerous clinical issues for the patient such as inflammation, unwanted blood clots and damage to tissue.

Polyisoprene synthetic rubber is becoming well accepted in the market thanks to the feel-fit which is similar to natural rubber latex. However, this material is manufactured with combinations of several chemicals, including accelerators, and contains high levels of residuals which are the origin of type IV allergies. In addition, the mechanical properties of the films, especially the tear resistance, is lower than other conventional materials such as polychloroprene or nitrile rubber and the gloves are reported to fail more easily than NRL during usage. U.S. Pat. No. 8,673,993 describes a technology to manufacture radiation crosslinked polyisoprene which has the potential to replace conventional accelerators by other crosslinking agents, therefore reducing the risk of developing type IV allergies. However, the crosslinked material still contains other chemicals and the film performance remains relatively poor.

Polychloroprene material has been used in the market for decades. Polychloroprene can be formulated with a different range of chemicals than those used for NR or IR, therefore offering superior alternatives in terms of skin tolerance. However, similar abietane derivatives are still present in their composition which remain a concern in terms of type IV allergies. Advantageously, CR offers stronger mechanical performance than polyisoprene and, when used in water dispersions, CR is also significantly cheaper. However, the material is significantly stiffer than polyisoprene or natural rubber, which represent a major drawback for wide acceptance in the surgical glove market.

Synthetic surgical gloves made of nitrile (NBR) have also been developed taking advantage of the outstanding mechanical performance (tensile strength, puncture and abrasion resistances) and low-cost formulation without the use of common accelerators. However, the performance of this type of carboxylic polymer is partially impaired by prolonged contact with aqueous or polar solvent which can affect the film barrier and mechanical properties. Also, as the material is extremely stiff it fails to find interest in the market.

Blends based on these common elastomers have also been developed to provide additional benefits in use. As an example, polyisoprene blended either with polychloroprene or with nitrile have been developed (United States Patent Application Publication No. 2006/0222688) which combine the "softness" of the polyisoprene with the "mechanical resistance" and comparatively "low cost" of polychloroprene and nitrile material. However, these blends still contain chemical accelerators that can generate type IV allergies.

Finally, other elastomers like Butyl Rubbers (IIR), Polyurethanes (PU), Fluoroelastomers (FKM), Styrene Butadiene Rubber (SBR) and the like could be employed, but only find selected applications primarily for industrial use.

To conclude, none of the conventional rubbers and rubber blends used in the glove industry, and especially in the surgical glove industry, can be formulated free of any accelerators with adequate mechanical resistance while offering the very soft feel required for surgical applications.

Styrenic Block Copolymers (SBCs) can offer this cleaner and softer alternative. SBCs are classified as thermoplastic elastomers and possess the mechanical properties of rubbers and the processing characteristics of thermoplastics. These properties result from their molecular structure: SBCs consist of at least three blocks, generally two hard polystyrene end blocks and one soft, elastomeric (polybutadiene, polyisoprene-hydrogenated or not) midblock. More common SBCs comprise linear triblock copolymers such as styrene-ethylene/butylene-styrene (SEBS), styrene-butadiene-styrene (SBS) and styrene-isoprene-styrene (SIS), styrene-[ethylene-(ethylene-propylene)]-styrene (SEEPS, obtained by hydrogenation of polyisoprene/butadiene), styrene-ethylene/propylene-styrene (SEPS), but other architectures (for example copolymers composed of more than three blocks) and other structures (star or radial) and polymer functionalization are also possible. Various architectures of SBCs can be envisaged such as star polymers with only some of the arms containing styrene. Significantly, SBCs with a saturated elastomeric mid-block offer enhanced mechanical properties and are more resistant to oxidative degradation.

For example, suitable compositions of SBCs for use in surgical gloves are described in the EP 0488021 which discloses a combination of two or more Styrene-Ethylene/Butylene-Styrene (S-EB-S) block copolymers, and EP 1472315 which discloses a combination of one S-EB-S block copolymer and one Styrene-EthylenePropylene-Styrene-EthylenePropylene (S-EP-S-EP) block copolymer. All these compositions are free of any chemical accelerators and can be formulated to be softer than any of the conventional rubbers described above. These two European patents describe the use of SBC with a saturated mid-block to provide gloves with improved resistance to oxidative degradation as compared with conventional rubbers used for medical gloves.

As another advantage, SBCs can be used in solvent casting, as these polymers can form solutions with acceptable viscosities that can be utilised for dipping. Solvent casting is a versatile technology that offers some distinct advantages over the conventional "water dispersion" manufacturing technology starting from latexes. The films cast from solvent can reach extremely high-quality requirements as the technology does not require any processing additives such as surfactants and resins that remain in the dry film. For example, abietane derivatives (which could be skin sensitizers) are commonly used in water-based (latex) technologies to provide better film-forming properties.

Consequently, gloves manufactured from solvent casting of SBCs show excellent barrier performance toward hydration, that is absorption of water, and improved electrical insulation performance can therefore be achieved.

However, SBCs possess two major shortcomings which have today limited their market potential, particularly for use in surgical gloves.

The first is linked to the type of crosslinking. As the network is made only of physical crosslinks of polystyrene, rather than chemical crosslinks, the glassy polystyrene domains soften and lose their cohesion when contacted with certain organic solvents and/or when exposed to temperatures above the glass transition temperature of the polystyrene, around 80-90° C. For example, surgical gloves made of SBCs are destroyed when placed in direct contact with organic solvents. Several organic solvents and "aggressive" chemicals may be used in the medical field, examples being methyl methacrylate monomer (MMA) which is present in uncured bone cement used in arthroplasty, and diethyl ether which is used as a solvent in some preparations, such as collodion. The weak chemical resistance of SBCs to these solvents is a major limitation of this family of elastomers for gloves for surgical usage.

The second is linked to the limited mechanical properties of these materials, especially the tensile, abrasion and tear resistance. It is believed to be linked to the nature of polymer, especially its relatively lower molecular weight compared to other synthetic polymers used in water dispersion, as well as the presence of significant amount of plasticizer. Therefore, some intrinsic mechanical properties of SBC can be inferior to other synthetic rubbers, such as for example the resistance of the material when exposed to abrasion which can create premature glove breaches.

Various additives can be used to improve the mechanical performance, such as tensile and tear resistance of the SBCs, up to a certain limit. Such additives can modify the morphology and the size of the phase separation. Typical additives are low molecular weight polymers miscible with the PS block, such as aromatic resins, and copolymers comprising a miscible block with the PS block such as styrene maleic anhydride resins (SMA) resins for example. Other additives can also be used to modify the film cohesion and generate tack of the SBCs composition but have limited interest for glove application.

As any conventional elastomer, unsaturated SBCs can also be chemically crosslinked to further improve chemical and thermal resistance. For example, SIS and SBS can be formulated with conventional vulcanization systems such as sulphur and accelerators. Other crosslinking mechanisms to vulcanization have also been described in the literature such as thiol-ene reaction of SBS in presence of a polythiol under UV (Decker et al., Journal of Applied Polymer Science, vol. 77, 1902-1912, 2000). Crosslinking of saturated SBCs such as SEBS has also been described using acrylates such as trimethylol propane trimethacrylate (TMPTM) under electron beam (Zurawski et al., Polymer Engineering and Science, 1983, vol. 23, 9).

These crosslinking mechanisms have the advantage in being "cleaner" compared to conventional vulcanization, as the crosslinking agent is incorporated into the polymeric network which is not the case for accelerators.

However, any form of additional chemical cross-linked to SBCs would change the structure and affect the properties, specifically it will reduce the flexibility.

Therefore, all the materials discussed above, inclusive of SBCs, have some limitations, and the need exists for an elastomeric article which exhibits durable barrier properties during use, enhanced flexibility and good biocompatibility, especially for surgical or industrial applications.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY

The present disclosure relates to a new class of multi-layered synthetic rubber compositions comprising at least two layers. The multi-layered compositions find particular use in the manufacture of thin walled articles, such as gloves.

In one aspect the present disclosure provides a multilayer composition comprising:
(a) a first layer comprising a styrene block copolymer (SBC) composition; and;
(b) a second layer comprising one or more synthetic elastomers and, optionally, one or more styrene block copolymers (SBCs).

Optionally, the multilayer composition comprises one or more further layers.

First Layer

In some embodiments the composition of SBC of the first layer comprises at least one SBC selected from the group consisting of so-called Styrenic Block Copolymers (SBCs) that includes, but is not restricted to, linear, radial or star SEBS, SEPS, SEEPS, SBSS (styrene-butadiene-styrene-styrene block copolymer), SIS, SBS, SIBS, and mixtures thereof. Various functionalisation and architectures of SBCs are envisaged such as star polymers with only some of the arms containing styrene.

Preferably, the SBC is composed of one or a mixture of SBCs of number average molecular weight (Mn) above 100,000 g/mol.

In another preferred embodiment, the SBC composition comprises polymers with a saturated mid-block which offer improved resistance to oxidative degradation.

In some embodiments the SBC composition of the first layer may comprise one or more plasticizers. The plasticizer is a molecule or blend of molecules that assist in enhancing the stretching and flexibility of the SBC. The plasticizer is preferentially one or more liquid saturated polyolefins compatible with the midblock (elastomeric block) of the SBC.

Preferred plasticizers are mineral oils, but the plasticizer can also be sourced from "green chemistry" for example vegetable oils, such as sunflower, rapeseed, coco oil or others. The plasticizer may also be an oligomer or other elastomer that possesses sufficient compatibility with the rubbery mid-blocks. Examples include, low molecular weight polybutadiene, polyisoprene, polyisobutene, amorphous polyolefin copolymers of propylene and ethylene, butyl rubber and other polymers known to have a sufficient compatibility with the rubbery block.

In some embodiments the SBC composition of the first layer comprises one or more reinforcing resins. The reinforcing resin is selected from components which can improve the mechanical performance (tensile and tear resistance) of the SBCs. Such components are typically low molecular weight polymers miscible with the PS block, such as aromatic resins, and copolymers comprising a block miscible with the PS block, such as styrene maleic anhydride (SMA) resins and ionomer resins. The reinforcement of the mechanical properties can also be provided by reinforcing fillers, such as reinforcing silica, carbon black fillers, fibres and so on.

In some embodiments the SBC composition of the first layer comprises other conventional rubber additives to provide the required physical aspect and mechanical performance of the finished material, such as, but not limited to: pigments, primary and secondary antioxidants, fillers (mineral or organic), vulcanization and crosslinking agents, photo-initiator, anti-static agents, anti-foam, surfactants, and other processing agents and resins.

In some embodiments the multilayer composition may also include functional additives which may be chosen so as to adjust the final properties desired for the glove. These functional additives may be chosen especially from anticorrosion agents, lubricants, chemical markers, phase-change products, energetic-particle (radiation) decelerators, agents with disinfecting power, odoriferous agents or moisturizers, dyes for detecting cuts, and combinations thereof.

The SBC composition is preferentially processed by dipping using solutions in solvents (solvent casting films). Alternatively, water dispersions (latexes) of SBC can also be used.

Second Layer

In some embodiments the synthetic elastomer of the second layer is selected from the group consisting of polychloroprene (CR), polyisoprene (IR), nitrile rubber (NBR), styrene butadiene rubber (SBR), butyl rubber (IIR), polyurethane (PUR) and combinations thereof.

The elastomer or blend of elastomers may, optionally, be blended with one or a blend of an SBC composition, in any proportion. Blends of synthetic elastomers without SBCs are also contemplated.

The elastomers may be utilized starting either from "dry rubbers", by dissolution in appropriate solvents and then solvent-casting a film or starting from water dispersions (latex), considering that both dry and latex dispersions of the above elastomers are currently available in the market.

The elastomer composition may contain all the conventional additives utilized to provide a thin film with the required physical and mechanical specifications.

These additives include, but are not limited to, plasticizers, reinforcing resins and fillers, crosslinking additives (vulcanization or/and other chemical crosslinker systems), primary and secondary antioxidants, processing resins and chemicals (surfactants, sodium hydroxide, etc), mold release agents, and so on.

Combinations of the various synthetic elastomers, in any proportions, may be employed.

In preferred embodiments of the present disclosure, the synthetic elastomer comprises a blend of CR and SBC, or a blend of IR and SBC, or a blend of CR and IR, or a blend of CR and NBR, or a blend of CR, NBR and SBC.

In another preferred embodiment, the synthetic CR is selected from general purpose Polychloroprenes, where n-dodecyl mercaptan or xanthogen disulphide may be used as a transfer agent during polymerization or alternatively a sulfur modified grade. A slow crystallization grade is preferred and may be selected from homopolymer of chloroprene (2-chlorobutadiene-1,3) or a copolymer of chloroprene and a comonomer (for example, 2,3-dichloro-1,3 butadiene).

In another preferred embodiment, the synthetic NBR is selected from latex dispersion of carboxylated nitrile butadiene rubber. This copolymer has a weight ratio of 25 to 39% of acrylonitrile and 3 to 12% of methacrylic acid.

In another preferred embodiment, the IIR is selected from a range of halobutyl (bromo or chloro) as opposed to unhalogenated butyl.

Surprisingly, the unique multi-layer compositions display particularly advantageous properties compared to elastomers on their own, or to blends described in the prior art. The combination of structures and material compositions offer advantageous performance and benefits which have not been previously described in glove applications. Surprisingly, the multi-layer compositions combine high flexibility with superior mechanical properties, while being cleaner overall because they require fewer crosslinking additives.

In this regard, the flexibility of the multilayer composition may be remarkably enhanced, particularly compared to CR, NBR, PUR and SBR, as well as the "cleanliness", especially compared to pure IR elastomer.

The multilayer composition may be made by superposition of several layers of the same composition or with different compositions.

In some embodiments the total thickness of the multilayer composition may be between about 10 microns and about 500 microns, preferably between about 50 microns and about 350 microns, more preferably between about 100 microns and about 300 microns.

In some embodiments the total thickness of the multilayer composition is less than 500 microns, or less than 400 microns.

In some embodiments the ratio of the thickness of the first layer to the thickness of the second layer is between about 2:1 to about 20:1, preferably between about 3:1 to about 10:1.

In some embodiments the multilayer composition comprises a first layer comprising SBC, for example SEBS, and the second layer comprises a blend of SBC (SIS) and IR, wherein the weight ratio of SIS to IR is greater than 50%.

In some embodiments the multilayer composition comprises a first layer comprising an SBC composition, for example SEBS, and the second layer comprises a blend of NBR and CR, wherein the weight ratio of CR to NBR is greater than 50%

The multilayer composition may find advantageous performance in various fields of application such as in medical or industrial glove use.

In another aspect the present disclosure provides an article of manufacture, such as a glove, comprising any one of the herein disclosed multi-layer compositions.

Preferably, a glove comprises layers having different compositions.

Advantageously the multilayer composition offers the possibility to laminate films made through different film-formation processes, for example using water dispersion (latex) or polymer solutions (solvent cast films).

In another aspect the present disclosure provides a process for manufacturing a multilayer composition according to any one of the herein disclosed embodiments, said process comprising the following steps:
(a) forming a layer of one or more synthetic elastomers on a mold; and
(b) subsequently forming a layer comprising an SBC composition on top of the layer of one or more synthetic elastomers.

Optionally, one or more further layers may be applied, either before step (a), between steps (a) and (b), or after step (b).

In a preferred embodiment, the synthetic elastomer layer is formed from a latex dispersion of the one or more synthetic elastomers. In another preferred embodiment the layer comprising an SBC composition is formed from a solution of the SBC composition.

The process may be performed by sequentially dipping the mold in a dispersion or solution of the one or more synthetic elastomers or SBC composition.

In the case of glove manufacture, it will be appreciated that after removing the finished glove from the mold, the synthetic elastomer layer represents the outside of the glove when the glove is in use.

In case of any incompatibility that may arise from the selection of the compositions in the two layers, one or more intermediate layers which may be a mixture of both of the compositions of the synthetic elastomer layer and SBC layer, optionally with addition of other adhesion promoters may be used to facilitate the lamination of the layers.

The adhesion between the layers may also be achieved through chemical or physical treatment. Chemical treatment is understood to mean either a grafting or a chemical attack, and physical treatment is understood to mean a bombardment of the surface of the film with ions, electrons (corona or plasma treatment) or photons (ultraviolet treatment).

Gloves also need to be easily donned, therefore the inside of the glove may be modified according to means known in the art such as fibre particles (flock lined gloves), textile fabric (supported gloves), donning without any free powder, such as polymer coating or surface modification (chlorination) or use of powder lubricant.

The article, for example glove, particularly the dried article, may subsequently be exposed to radiation, for example electron beam, gamma, UV or X-Ray radiation.

Further features and advantages of the present disclosure will be understood by reference to the following drawings and detailed description.

BRIEF DESCRIPTION OF THE DRAWINGS

FIG. 1 is flow chart outlining a process for making a glove according to one embodiment of the present disclosure.

DETAILED DESCRIPTION OF THE EMBODIMENTS

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any methods and materials similar or equivalent to those described herein can also be used in the practice or testing of the present disclosure, the preferred methods and materials are now described.

It must also be noted that, as used in the specification and the appended claims, the singular forms 'a', 'an' and 'the' include plural referents unless otherwise specified. Thus, for example, reference to a 'SBC' may include more than one SBCs, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

Unless specifically stated or obvious from context, as used herein, the term 'about' is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Any methods or processes provided herein can be combined with one or more of any of the other methods or processes provided herein.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

In medical glove applications, a multilayer composition comprising a first layer of SBC (SEBS) and a second layer comprising a blend of SBC (SIS, 80%) and IR (20%)

advantageously offers the required level of chemical resistance, while maintaining the excellent flexibility and dexterity provided by the SBC.

In industrial applications, electrical insulating gloves designed for enhanced electrical insulation protection may comprise a multi-layer composition, wherein the first layer comprises an SBC composition, advantageously SEBS. The SBC layer may be prepared by solvent casting. The second layer comprises a blend of NBR (30%) and CR (70%). The multi-layer material provides superior feel-fit and dexterity performance to products currently in the marketplace. The blend of NBR and CR provides protection to the SBC first layer performance against mechanical and chemical aggression while the first layer provides the electrical insulation protection and the resistance to degradative oxidation, especially ozone.

Example 1: Multilayer Composition Comprising a First Layer of SEBS with a Second Layer of a Latex Blend CR/NBR So that the manner in which the above recited features of the present disclosure can be illustrated a brief description of a process flowchart is depicted in FIG. 1. It is to be noted, however, that the flowchart and disclosure depict exemplary embodiments of the disclosure and are therefore not to be considered as limiting the scope of the disclosure.

In this example to illustrate the present disclosure, cleaned glove formers may be dipped in a coagulant mixture of calcium nitrate, a non-ionic wetting agent such as an ethoxylated fatty alcohol and a release agent, for example calcium carbonate or a stearate salt, wax and silicone dispersed in water.

The coagulant on the formers may then be dried and dipped in a latex composition (synthetic elastomers): in this example a mixture of polychloroprene (CR) and a carboxylated butadiene nitrile (NBR) may be used and compounded as outlined in Table 1.

TABLE 1

| compounding of latex blend of CR and NBR latex | |
|---|---|
| Ingredient | phr |
| CR Latex | 70 |
| NBR Latex | 30 |
| Sodium dodecylbenzene sulfonate (SDBS) | 0.3 |
| Sodium Hydroxide | 0.2 |
| ZnO | 3.5 |
| Butylated reaction product of p-cresol and dicyclopentadiene (antioxydant) | 1 |
| Zinc dithiocarbamate (ZDEC) | 1 |
| Sulfur | 1 |

The film formed at the surface of the glove former may then be leached in hot water, crosslinked by heating in an oven, leached, then dried clean, so the surface is free from any contamination for the next dipping.

The next dipping may comprise a coating of a plasticized Styrene Ethylene butadiene Styrene block copolymer composition obtained by solubilization of this elastomer and plasticizer (mineral oil) in a solvent. The viscosity of a solution suitable for dipping is typically within a range of 500 to 2000 cps.

The operations of coating and subsequent drying prior to any next dipping may be repeated to achieve the required thickness of SEBS and then completed with an extended drying to complete the evaporation of any trace of residual solvent. In the present example, the thickness ratio of first layer to second layer (SEBS layer) will be about 1:5.

A lubricating coating applied by dip coating would finish the glove structure. This coating may be compounded from a mixture of different ingredients that would enhance the donning of the glove: typically, a mixture of acrylate base copolymer, wax and silicone.

In this example it is envisaged that the glove would offer the following unique advantages which combine a superior mechanical resistance from the external layer made of a chemically crosslinked CR/NBR blend, which will additionally withstand mild exposure to chemicals, such as aromatic hydrocarbon solvent (for example, toluene) or ethylene chloride, which would solubilize SEBS.

This laminated glove would also be highly flexible. A modulus at 100% elongation is a good indicator of flexibility and it is expected that the glove presents a high level of flexibility and hence dexterity for the user compared with the performance of blended latex (CR/NBR) composition or any other composition made of pure CR or NBR mixture.

The core of the glove made of SEBS by solvent dip coating may also impart unique characteristics to the laminated glove while being protected by a strong external layer made from the CR/NBR blend.

SEBS dipped as a true solution also imparts the highest level of impermeability (avoiding problem of pinholes). It is impervious to cracking, from ozone or ageing condition, due to its saturated nature and contains no surfactant nor any substances that would promote hydration and impair resistivity. Such a glove would advantageously find interest in the field of insulating gloves.

In addition, such composition may offer a reduced level of accelerator which is only 20% of that of a traditional latex dipped product.

Example 2: Multilayer Composition Comprising a First Layer of SEBS with a Second Layer of a Latex Blend IR/SIS This multilayer material comprises a first layer of SEBS (same composition to example 1), and a second layer comprising a blend of SIS (80%) and IR (20%). The thin layer may be crosslinked using a conventional sulfur crosslinking system.

The contents of all references, and published patents and patent applications cited throughout the application are hereby incorporated by reference. Those skilled in the art will recognize that the disclosure may be practiced with variations on the disclosed structures, materials, compositions and methods, and such variations are regarded as within the ambit of the disclosure.

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described.

Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A multilayer article comprising:
   (a) a first layer comprising a styrene block copolymer (SBC) composition, said styrene block copolymer (SBC) composition comprising one or a mixture of SBCs of number average molecular weight (Mn) above 100,000 g/mol;
   (b) a second layer comprising one or more synthetic elastomers; and
   (c) optionally, one or more further layers;
   wherein the synthetic elastomer comprises a blend of chloroprene (CR) and styrene block copolymer (SBC), or a blend of polyisoprene (IR) and styrene block copolymer (SBC), or a blend of chloroprene (CR) and polyisoprene (IR), or a blend of chloroprene (CR) and nitrile rubber (NBR), or a blend of chloroprene (CR), nitrile rubber (NBR) and styrene block copolymer (SBC).

2. The multilayer article according to claim 1, wherein the SBC composition of the first layer comprises at least one SBC selected from the group consisting of linear, radial or star styrene-ethylene/butylene-styrene block copolymer (SEBS), styrene-ethylene/propylene-styrene block copolymer (SEPS), styrene-[ethylene-(ethylene-propylene)]-styrene block copolymer (SEEPS), styrene-butadiene/styrene-styrene block copolymer (SB SS), styrene-isoprene-styrene block copolymer (SIS), styrene-butadiene-styrene block copolymer (SBS), styrene-isoprene/butadiene-styrene block copolymer/SIBS), and combinations thereof.

3. The multilayer article according to claim 1, wherein the styrene block copolymer (SBC) of the first layer comprises styrene block copolymer (SBC) with a saturated elastomeric mid-block.

4. The multilayer article according to claim 1, wherein the styrene block copolymer (SBC) composition of the first layer further comprises one or more plasticizers.

5. The multilayer article according to claim 4, wherein the plasticizer comprises a liquid or a mixture of liquid saturated polyolefins compatible with a saturated elastomeric mid-block of the styrene block copolymer (SBC).

6. The multilayer article according to claim 4, wherein the plasticizer is selected from one or more vegetable oils, or oligomeric or elastomeric polybutadiene, polyisoprene, polyisobutene, amorphous polyolefin copolymers of propylene and ethylene, and butyl rubber.

7. The multilayer article according to claim 1, wherein the styrene block copolymer (SBC) composition of the first layer further comprises one or more reinforcing resins and/or fillers.

8. The multilayer article according to claim 7, wherein the reinforcing resin is one or more aromatic resins miscible with a styrene block of the styrene block copolymer (SBC), or copolymers comprising a block miscible with a styrene block of the styrene block copolymer (SBC), or ionomer resins, and/or wherein the reinforcing filler is one or more of reinforcing silica, carbon black fillers, and fibres.

9. The multilayer article according to claim 1, wherein the styrene block copolymer (SBC) composition of the first layer further comprises conventional rubber additives, selected from, pigments, primary and secondary antioxidants, fillers, vulcanization and crosslinking agents, photo-initiator, anti-static agents, anti-foam, surfactants, and combinations thereof.

10. The multilayer article according to claim 1, wherein the styrene block copolymer (SBC) composition of the first layer further comprises functional additives selected from anticorrosion agents, lubricants, chemical markers, phase-change products, energetic-particle decelerators, agents with disinfecting power, odoriferous agents or moisturizers, dyes for detecting cuts, and combinations thereof.

11. The multilayer article according to claim 1, wherein the synthetic elastomer further comprises one or more additives selected from plasticizers, reinforcing resins and fillers, crosslinking additives, primary and secondary antioxidants, processing resins and chemicals, or mold release agents.

12. The multilayer article according to claim 1, wherein the first layer comprises styrene block copolymer (SBC), and the second layer comprises a blend of styrene block copolymer (SBC) and polyisoprene (IR), wherein the weight ratio of styrene block copolymer (SBC) to polyisoprene (IR) is greater than 50%.

13. The multilayer article according to claim 1, wherein the first layer comprises styrene block copolymer (SBC) composition, and the second layer comprises a blend of nitrile rubber (NBR) and chloroprene (CR), wherein the weight ratio of chloroprene (CR) to nitrile rubber (NBR) is greater than 50%.

14. The multilayer article according to claim 1, wherein the chloroprene (CR) is selected from homopolymer of chloroprene (2-chlorobutadiene-1,3) or a copolymer of chloroprene and a comonomer (2,3-dichloro-1,3 butadiene).

15. The multilayer article according to claim 1, wherein the total thickness of the multilayer article is between about 10 microns and about 500 microns.

16. The multilayer article according to claim 1, wherein the total thickness of the multilayer article is less than 500 microns.

17. The multilayer article according to claim 1, wherein the ratio of the thickness of the first layer to the thickness of the second layer is between about 2:1 to about 20:1.

18. An article of manufacture comprising a multilayer article according to claim 1.

19. The article of manufacture according to claim 18, wherein the article is a glove.

* * * * *